(12) United States Patent
Klesse et al.

(10) Patent No.: US 9,656,941 B2
(45) Date of Patent: May 23, 2017

(54) METHOD FOR PRODUCING METHACRYLATED BENZOPHENONES

(71) Applicants: Wolfgang Klesse, Mainz (DE); Joachim Knebel, Alsbach-Haehnlein (DE); Doris Saal, Bensheim (DE)

(72) Inventors: Wolfgang Klesse, Mainz (DE); Joachim Knebel, Alsbach-Haehnlein (DE); Doris Saal, Bensheim (DE)

(73) Assignee: Evonik Roehm GmbH, Darmstadt (DE)

( * ) Notice: Subject to any disclaimer, the term of this patent is extended or adjusted under 35 U.S.C. 154(b) by 0 days.

(21) Appl. No.: 15/026,861

(22) PCT Filed: Sep. 29, 2014

(86) PCT No.: PCT/EP2014/070787
§ 371 (c)(1),
(2) Date: Apr. 1, 2016

(87) PCT Pub. No.: WO2015/049200
PCT Pub. Date: Apr. 9, 2015

(65) Prior Publication Data
US 2016/0297738 A1   Oct. 13, 2016

(30) Foreign Application Priority Data

Oct. 4, 2013   (DE) .................. 10 2013 220 127

(51) Int. Cl.
| | |
|---|---|
| *C07C 67/08* | (2006.01) |
| *C07C 67/62* | (2006.01) |
| *C08F 22/14* | (2006.01) |
| *B01J 31/02* | (2006.01) |
| *B01J 31/04* | (2006.01) |
| *C08F 2/50* | (2006.01) |

(52) U.S. Cl.
CPC ........... *C07C 67/08* (2013.01); *B01J 31/0209* (2013.01); *B01J 31/04* (2013.01); *C07C 67/62* (2013.01); *C08F 22/14* (2013.01)

(58) Field of Classification Search
CPC .. C08F 2/50; C08F 22/14; C07C 67/08; B01J 31/02; B01J 31/0209; B01J 31/04
USPC .............. 522/34, 905; 526/75, 326; 560/221
See application file for complete search history.

(56) References Cited

U.S. PATENT DOCUMENTS 4,737,559 A * 4/1988 Kellen .................... A61L 15/58
                                                            522/154
2011/0196169 A1    8/2011 Knebel et al.

FOREIGN PATENT DOCUMENTS

| DE | 10 2008 054 611 A1 | 6/2010 |
|---|---|---|
| JP | 2003-261506 A | 9/2003 |
| JP | 2003-261556 A | 9/2003 |

OTHER PUBLICATIONS

Machine translation of JP 2003-261506A; publication date: Sep. 2003.*
International Search Report issued Feb. 2, 2015, in PCT/EP2014/070787 filed Sep. 29, 2014.

* cited by examiner

*Primary Examiner* — Fred M Teskin
(74) *Attorney, Agent, or Firm* — Oblon, McClelland, Maier & Neustadt, L.L.P.

(57) ABSTRACT

The invention relates to a process for preparing methacrylic esters of hydroxyl-functional benzophenones and to their use. Methacrylated benzophenones (benzophenone (meth) acrylates) can be prepared in high purity by the process of the invention, in a simple way and in a high yield.

20 Claims, No Drawings

METHOD FOR PRODUCING METHACRYLATED BENZOPHENONES

DESCRIPTION

The invention relates to a process for preparing methacrylic esters of hydroxyl-functional benzophenones and to their use. Methacrylated benzophenones can be prepared in high purity by the process of the invention, in a simple way and in a high yield.

Described in the prior art is a methacrylic anhydride process for the preparation of the abovementioned esters (JP 2003261506, Mitsubishi Rayon). Triethylamine is used as catalyst. Since the amine forms a salt of the methacrylic acid produced during the reaction, the amine must be made equimolar with the benzophenone. Correspondingly, equimolar amounts of salt are obtained, and have to be disposed of as waste. The economics of the process are therefore poor. Other methods in the prior art are the reaction of methacryloyl chloride with hydroxy-functional benzophenone, and the reaction of this raw material with glycidyl methacrylate. Operating with methacryloyl chloride means that the corrosive and caustic properties must be heeded. On contact with water, moreover, HCl is released.

DE 1720603 describes a process for preparing aqueous dispersions of readily crosslinkable polymers. It involves copolymerizing acrylic and methacrylic esters with photoactive, olefinically unsaturated monomers, including benzophenone derivatives, with optional accompanying use of photoactive, nonionic emulsifiers.

EP 0346788 describes a process for preparing radiation-sensitive carbamoylbenzo- and -acetophenones having at least one methacrylate or acrylate end group. It involves reacting isocyanatoalkyl (meth)acrylates with hydroxyacetophenones or hydroxybenzophenones, using a basic catalyst. Here it is necessary to operate in the absence of moisture. Moreover, only dried, non-nucleophilic solvents can be used.

WO 2010/072479 describes the preparation of the abovementioned esters in the presence of catalytic amounts of sulphuric acid. When reaction is at an end, the catalyst has to be neutralized with aqueous sodium hydroxide solution, and the sodium sulphate has to be removed by filtration.

In the case of the salt-catalyzed esterification, the alcohol to be esterified is reacted with the carboxylic anhydride in the presence of small amounts of salt of the acid on which the anhydride is based. According to DE 3601098 or Autorenkollektiv, Organikum, 20th edn. 1999, pp. 444-445, it is possible in this way to esterify sugars to the acetates in the presence of acetic anhydride and sodium acetate. However, large amounts of a catalyst and/or of acylating agent are required. Dithranol, which is similar to 4-hydroxybenzophenone, is reacted with 20% of its molar amount of anhydride, or must be acetylated using a 3.3-fold molar excess of acetic anhydride in the presence of sodium acetate (H. P. Faro et al., Arch. Pharm. 313, 800 (1980)). In the esterification of sugars, a large excess of acylating agent is employed (1.76 mol/mol).

It was an object of the invention, therefore, to provide a further-simplified preparation process wherein the catalyst can be removed without additional steps, such as neutralization, for example, and wherein the accompanying salt load is low.

The object is achieved by means of a process for preparing benzophenone (meth)acrylates, characterized in that hydroxybenzophenone and (meth)acrylic anhydride are reacted in the presence of catalytic amounts of salt, the molar ratio of (meth)acrylic anhydride to hydroxybenzophenone being 1.0:1.0 to 1.6:1.0.

The (meth)acrylate notation here denotes both methacrylate, such as methyl methacrylate, ethyl methacrylate, etc., and acrylate, such as methyl acrylate, ethyl acrylate, etc. and also mixtures of both.

Surprisingly it has been found that a high degree of conversion can be achieved with the process of the invention. The process of the invention also involves only a low salt load. The salt is easy to separate off.

In one particular embodiment, the (meth)acrylic acid produced as by-product is used as comonomer in a subsequent polymerization of the benzophenone monomer. In another embodiment, the (meth)acrylic acid is recycled for the preparation of new (meth)acrylic anhydride.

In one preferred embodiment, the molar ratio of (meth)acrylic anhydride to hydroxybenzophenone is situated in the range from 1.0:1.0 to 1.6:1.0. In another embodiment, the ratio is situated in the range from 1.1:1.0 to 1.4:1.0, more preferably in the range from 1.1:1.0 to 1.2:1.0. Very preferably the molar ratio of (meth)acrylic anhydride to hydroxybenzophenone is 1.1:1.0.

One embodiment uses a plurality of hydroxybenzophenones. Particularly preferred in this case are hydroxybenzophenones selected from the group consisting of 4-, 3- or 2-hydroxybenzophenone and/or their isomer mixtures or other mixtures, and also difunctional hydroxybenzophenones such as 2,3-, 2,4- or 4,4'-dihydroxybenzophenones and/or their isomer mixtures or other mixtures.

Another embodiment uses mixtures of methacrylic anhydride and acrylic anhydride.

In one particular embodiment, 4-hydroxybenzophenone is reacted with methacrylic anhydride to give 4-(methacryloyloxy)benzophenone.

In one preferred embodiment, sodium acetate is used as catalyst. Also suitable are corresponding lithium or potassium acetates and/or Li, Na or K (meth)acrylates. Particular preference is given to using Na methacrylate. In another embodiment, the stated salts are generated in situ from the corresponding methoxides and/or from their methanol solutions, during the reaction, from added acetic acid and/or from the (meth)acrylic anhydride present.

The corresponding salts may alternatively be added to the reaction following separate preparation.

In one preferred embodiment, the catalyst is used in an amount of 0.2 to 5.0 mol %, based on the amount of substance of the (meth)acrylic anhydride used. In another embodiment, the catalyst is used in an amount of 0.3 to 4.0 mol %, preferably of 0.45 to 2.5 mol %, more preferably of 0.5 to 2.3 mol % or up to 0.7 mol %, based on the amount of substance of the (meth)acrylic anhydride used. In one particularly preferred embodiment, the catalyst is used in an amount of 0.5 mol %, based on the amount of substance of the (meth)acrylic anhydride used.

With the process of the invention, benzophenone (meth)acrylates can be obtained in solid form. In one preferred embodiment, the hydroxybenzophenone or hydroxybenzophenones are reacted with the (meth)acrylic anhydride or anhydrides at a temperature in the range from 50 to 120° C., more preferably in the range from 70 to 110° C., more preferably still in the range from 85 to 95° C. or 90 to 100° C., very preferably at 90° C.

The reaction time, in particular at 90° C., is preferably 1 to 13 h, more preferably 1.5 to 11 h, more preferably still 4 to 8 h.

The subsequent work-up of the crude monomer takes place, optionally after the hydrolysis of the excess (meth)

acrylic anhydride, for example by addition of methanol or by stirred incorporation into water. In this way, the water-soluble impurities are dissolved and can be separated off readily. Benzophenone (meth)acrylate is precipitated from the water and isolated in solid form by filtration.

The benzophenone (meth)acrylates, which are prepared in high purity, can be stored in solution with methyl methacrylate, n-butyl methacrylate, isobutyl methacrylate or styrene, and reacted further.

With the process of the invention it is likewise possible to obtain benzophenone (meth)acrylates in an alkyl (meth) acrylate solution. Other suitable solutions are styrene solutions. In one preferred embodiment the hydroxybenzophenone or hydroxybenzophenones are first mixed with the (meth)acrylic anhydride or anhydrides, catalyst and optionally stabilizers. Then the desired reaction temperature is set. In one preferred embodiment, the hydroxybenzophenone or hydroxybenzophenones are reacted with the (meth)acrylic anhydride or anhydrides at a temperature in the range from 50 to 120° C., more preferably in the range from 70 to 110° C., more preferably still in the range from 85 to 95° C. or 90 to 100° C., very preferably at 90° C. To produce the stated solution in alkyl (meth)acrylates, after reaction has taken place, alkyl (meth)acrylate and/or, optionally, mixtures thereof are added in order to obtain the desired concentration of benzophenone (meth)acrylate. Salts and impurities are separated off after this, using a suitable pressure filter.

The reaction time, particularly at 90° C., is preferably 2 to 8 h, more preferably 3 to 7 h, more preferably still 4 to 8 h, more particularly 4.5 to 5.5 h.

The alkyl (meth)acrylate is preferably selected from the group consisting of methyl (meth)acrylate, n-butyl methacrylate or isobutyl methacrylate. Also suitable, furthermore, are hydroxyalkyl (meth)acrylates, more particularly hydroxyethyl (meth)acrylate and/or hydroxypropyl (meth) acrylate. Particularly preferred is methyl methacrylate (MMA).

Subject matter of the patent is therefore also the preparation of a solution of benzophenone (meth)acrylates in alkyl (meth)acrylates or in styrene. In one preferred embodiment, 4-(methacryloyloxy)benzophenone is prepared in a 30% strength MMA solution.

Benzophenone (meth)acrylates can be used for the subsequent photocrosslinking of polymers by daylight or UV light, and also as polymeric photoinitiators.

The benzophenone (meth)acrylates may be used, moreover, as monomers and/or comonomers for polymerization reactions.

The examples which follow are intended to elucidate the invention in more detail, but do not confine it to the features disclosed herein.

EXAMPLES

Abbreviations:
MAAH (meth)acrylic anhydride
MeOH methanol
MMA methyl methacrylate
MAA methacrylic acid
NM30 solution sodium methoxide, 30% strength in methanol, from Evonik
GC area % area percentages by gas chromatography
GC; wt % weight percentages by gas chromatography
HQME hydroquinone monomethyl ether
AN acid number in mg KOH/g
Topanol A 2,4-dimethyl-6-tert-butylphenol (polymerization inhibitor)

Gas-chromatographic analysis: Instrument: Agilent 7820A with FID
Capillary column DB5, 30 m long, diameter 0.25 mm, layer thickness 0.25 pm
Injector temperature 250° C., detector temperature 300° C.
Temperature programme: 80° C. for 2 min, then heat at 16° C./min to 300° C., and hold this temperature for 6 min.

Example 1

Sodium Methacrylate Catalyst Generated In Situ

Apparatus: 2 l four-necked round-bottom flask with mechanical stirring, reflux condenser, air inlet, Pt100 temperature sensor, oil bath.

Batch: 1.5 mol (297.9 g) of 4-hydroxybenzophenone, 1.65 mol (270.3 g) of MAAH, 0.0087 mol (1.6 g) of NM30 solution, 399 mg of 2,4-dimethyl-6-tert-butylphenol (Topanol A);

Preparation of a 30% strength solution of 4-(methacryloyloxy)benzophenone in MMA: Addition of a total of 772 g of MMA Theoretical yield of 4-(methacryloyloxy)benzophenone: 399 g Procedure: 4-Hydroxybenzophenone was weighed out, and 126 g of the subsequently required MMA were added; a readily stirrable composition was formed. Then MAAH, Topanol A stabilizer and NM30 catalyst were added, air was introduced, and the batch was heated to 90° C. The course of the reaction was monitored by gas chromatography (a sample (approximately 1.5 ml) taken, diluted with approximately 5 ml of acetone, and filtered). After a total of 5 h at 90° C., the batch was cooled to 60° C., 30 g of methanol were added for conversion of the remaining MAAH, and the batch was stirred 60° C. for 1 h. The remainder of the MMA (646 g) was then added to the batch, to produce a 30% strength solution. After cooling with accompanying stirring, filtering took place through a pressure filter with Seitz T1000 filter layer (Ø14 cm). Yield: 1320.4 g Analyses:
Water content according to Karl Fischer: 0.03%
Topanol A: 538 ppm
GC area %: 52.543% MMA
9.491% MAA
0.829% 4-hydroxybenzophenone
0.701% 4-acetoxybenzophenone
34.921% 4-(methacryloyloxy)benzophenone
GC; wt %: MMA 57.9%
MAA 10.9%
4-(methacryloyloxy)benzophenone 28.5%
Hazen colour number: 315
AN: 69=10.58% MAA Example 2

Preparation of 4-(methacryloyloxy)benzophenone as Solid with Sodium Methacrylate Catalyst Produced In Situ Apparatus: see Example 1
Batch: 4.0 mol (794.7 g) of 4-hydroxybenzophenone, 4.4 mol (723.7 g) of MAAH, 0.0228 mol (4.2 g) of NM30 solution, 1055 mg of Topanol A;
Theoretical yield: 4-(methacryloyloxy)benzophenone: 1055.2 g Procedure: The batch was weighed out completely and then heated to 90° C. After a reaction time of 6 h, the 4-hydroxybenzophenone fraction was still 2.2% (GC analysis); a further 2 ml of NM30 solution was added and heating was continued.

After a total of 11 h at 90° C., the batch was cooled to 60° C. and 80 g of methanol were added for esterification of the unreacted MAAH. The batch was subsequently stirred at 60° C. for 1 h. Then the batch was poured with stirring (metal paddle stirrer, stirring motor) as a thin stream into 3 l of water. After 0.5 h of stirring, the precipitate was isolated by suction filtration on a glass filter frit, washed once again with 2.0 l of water (stirred for 30 minutes in a glass beaker with a stirring motor with metal paddle stirrer) and then dried with suction on the suction filter. The solid was subsequently dried to constant mass in air. Yield: 1042.3 g Analyses:
  Water content (Karl Fischer): <0.1%
  Topanol A: 808 ppm
  GC: 0.066% MAA
    1.239% 4-hydroxybenzophenone
    1.785% 4-acetoxybenzophenone
    95.574% 4-(methacryloyloxy)benzophenone
  Hazen colour number, 20% strength in acetone: 154

Example 3

Preparation of 4-(methacryloyloxy)benzophenone as Solid with Separately Prepared Sodium Methacrylate Catalyst Apparatus: see Example 1
Batch: 0.5 mol (99.4 g) of 4-hydroxybenzophenone, 0.55 mol (88.3 g) of MAAH, 0.0125 mol (1.35 g) of sodium methacrylate, 133 mg of HQME, 133 mg of Topanol A;
Theoretical yield of 4-(methacryloyloxy)benzophenone: 133.15 g Procedure: The batch was weighed out completely and then heated to 90° C. with introduction of air. The conversion was monitored by means of gas chromatography (GC). Composition after 1.5 h: 18.42% MAA, 2.5% MAAH, 0.83% hydroxybenzophenone, 75.84% 4-(methacryloyloxy) benzophenone. Cooling took place to 60° C., methanol (10 g) was added, and the batch was stirred at 60° C. for 1 h.

Then the batch was poured with stirring (metal paddle stirrer, stirring motor) as a thin stream into 500 ml of water. After 0.5 h of stirring, the precipitate was isolated by suction filtration on a glass filter frit, washed twice again with 500 ml of water (stirred for 15 minutes each time in a glass beaker with a stirring motor with metal paddle stirrer) and then dried with suction on the suction filter. The solid was subsequently dried to constant mass in air. Yield: 131.1 g Analyses:
  Water content according to Karl Fischer: 0.21%
  HQME: 13 ppm
  Topanol A: 1305 ppm
  GC: 0.012% MMA
    0.331% MAA
    1.573% 4-hydroxybenzophenone
    94.594% 4-(methacryloyloxy)benzophenone
  Colour number, 20% strength in acetone: 82

Example 4

Preparation of 4-(methacryloyloxy)benzophenone with Sodium Methacrylate Catalyst; Conversion Control Apparatus: see Example 1
Batch: 0.5 mol (99.4 g) of 4-hydroxybenzophenone, 0.55 mol (88.3 g) of MAAH, 0.003 mol (0.32 g) of sodium methacrylate, 133 mg of HQME, 133 mg of Topanol A;
Theoretical yield of 4-(methacryloyloxy)benzophenone: 133.15 g Procedure: The batch was weighed out completely and then heated to 90° C. The conversion was monitored by means of GC.

Composition in wt %:

| Reaction time | MAA | MAAH | Hydroxybenzophenone | 4-(Methacryloyloxy)benzophenone |
|---|---|---|---|---|
| 1 h | 16.69 | 6.47 | 4.66 | 69.72 |
| 2 h | 18.03 | 4.39 | 2.83 | 72.07 |
| 3 h | 18.95 | 3.46 | 1.21 | 73.96 |
| 4 h | 17.69 | 2.96 | 1.25 | 74.88 |

Cooling took place to 60°, methanol (9.6 g) was added to esterify the remaining

MAAH, and the batch was stirred at 60° C. for 1 h. Then the batch was poured with stirring (metal paddle stirrer, stirring motor) as a thin stream into 500 ml of water. After 0.5 h of stirring, the precipitate was isolated by suction filtration on a glass filter frit, washed twice again with 500 ml portions of water (stirred for about 15 minutes each time in a glass beaker with a stirring motor with metal paddle stirrer) and then dried with suction on the suction filter.

The solid was subsequently dried to constant mass in air. Yield: 136.7 g

Analyses:
  H2O: 0.25%
  HQME: 15 ppm
  Topanol A: 1530 ppm
  GC: 1.064% MAA
    2.571% 4-hydroxybenzophenone
    92.754% 4-(methacryloyloxy)benzophenone
  Colour number, 20% strength in acetone: 144

Example 5

Sodium Acetate Catalyst

Apparatus: 2 l four-necked round-bottom flask with mechanical stirrer, reflux condenser, air inlet tube and Pt100 temperature sensor, oil bath Batch:
  0.5 mol of 4-hydroxybenzophenone, purity 99.9%=99.2 g
  0.55 mol of methacrylic anhydride, purity 97.7%=86.9 g
  0.0125 mol of sodium acetate, anhydrous=1.025 g
  Topanol A=93.2 mg
  For esterifying the excess methacrylic acid: 9.6 g of methanol Theoretical yield of 4-(methacryloyloxy)benzophenone: 133.2 g Procedure: 4-Hydroxybenzophenone was weighed out. Methacrylic anhydride, Topanol A and sodium acetate were then added and the batch was subsequently heated to 90° C. with supply of air. It was stirred for 6 h, then cooled to 60°

C., and the methanol for esterifying the remaining methacrylic anhydride was added. Stirring took place for a further 1 h at 60° C. The batch was then introduced with stirring to 500 ml of $H_2O$, stirred for 0.5 h, filtered with suction, and the solid was washed once again with 500 ml of water in a glass beaker, and then dried with suction on the suction filter. The product was dried in air.

Yield: 130 g of 4-(methacryloyloxy)benzophenone

Analyses:

Water content: 0.36% Topanol A: 1390 ppm

Hazen colour number (10% in acetone): 16

GC area %: 0.011% MMA 0.650% MAA 1.834% 4-hydroxybenzophenone 2.928% 4-acetoxybenzophenone 91.560% 4-(methacryloyloxy)benzophenone

The invention claimed is:

1. A process for preparing a benzophenone (meth)acrylate, comprising:
    reacting a hydroxybenzophenone and a (meth)acrylic anhydride in the presence of a catalytic amount of a salt;
    wherein the molar ratio of (meth)acrylic anhydride to hydroxybenzophenone is in the range from 1.0:1.0 to 1.6:1.0; and
    wherein the salt is present in an amount of 0.2 to 5.0 mol % relative to the amount of (meth)acrylic anhydride.

2. The process according to claim 1, wherein the molar ratio is in the range from 1.05:1.0 to 1.5:1.0.

3. The process according to claim 1, wherein the hydroxybenzophenone is 4-hydroxybenzophenone.

4. The process according to claim 1, wherein the (meth)acrylic anhydride is methacrylic anhydride or acrylic anhydride.

5. The process according to claim 1, wherein the salt is sodium methacrylate.

6. The process according to claim 1, wherein the salt is present in an amount of 0.2 to 0.7 mol % relative to the amount of (meth)acrylic anhydride.

7. The process according to claim 1, wherein the reacting, takes place at a temperature in the range from 50 to 120° C.

8. The process according to claim 1, wherein the reacting takes place over 1 to 13 h.

9. The process according to claim 1, wherein the benzophenone (meth)acrylate is precipitated in water.

10. The process according to claim 1, wherein the benzophenone (meth)acrylate is employed as a monomer, a comonomer, or both in a polymerization process.

11. The process according to claim 1, wherein the benzophenone (meth)acrylate is employed as a photocrosslinker of a polymer.

12. The process according to claim 1, wherein the benzophenone (meth)acrylate is employed as a polymeric photoinitiator.

13. The process according to claim 1, further comprising at least one selected from the group consisting of
    quenching by contacting with water to precipitate the benzophenone (meth)acrylate, and
    esterifying unreacted (meth)acrylic anhydride by the addition of methanol.

14. A process for preparing a benzophenone (meth)acrylate, comprising:
    reacting a hydroxybenzophenone and a (meth)acrylic anhydride in the presence of a catalytic amount of a salt;
    wherein the molar ratio of (meth)acrylic anhydride to hydroxybenzophenone is 1.0:1.0 to 1.6:1.0; and
    wherein the salt is selected from the group consisting of sodium acetate, lithium acetate, potassium acetate, lithium (meth)acrylate, sodium eth acrylate, potassium (meth)acrylate and mixtures thereof.

15. The process according to claim 14, wherein the salt is sodium methacrylate.

16. The process according to claim 14, wherein the salt is present in an amount of 0.2 to 5.0 mol % relative to the amount of (meth)acrylic anhydride.

17. The process according to claim 14, wherein the molar ratio of (meth)acrylic anhydride to hydroxybenzophenone is 1,0:1,0 to 1.2:1.0.

18. The process according to claim 15, wherein the sodium (meth)acrylate is generated in situ from sodium methoxide.

19. A process for preparing a benzophenone (meth)acrylate, comprising:
    reacting a hydroxybenzophenone and a (meth)acrylic anhydride in the presence of a catalytic amount of a salt selected from the group consisting of sodium acetate, lithium acetate, potassium acetate, lithium (meth)acrylate, sodium (meth)acrylate. potassium (meth)acrylate and mixtures thereof; and
    quenching by contacting with water to precipitate the benzophenone (meth)acrylate.

20. The process according to claim 19, further comprising:
    esterifying unreacted (meth)acrylic anhydride by the addition of methanol prior to the quenching.

* * * * *